United States Patent [19]

Krief et al.

[11] Patent Number: 5,004,840
[45] Date of Patent: Apr. 2, 1991

[54] NOVEL PROCESS FOR PREPARING SEMI-CARONIC ALDEHYDES

[75] Inventors: Alain Krief, Wepion; Willy Dumont, Salet-Anhee, both of Belgium

[73] Assignee: Roussel Uclaf, Paris, France

[21] Appl. No.: 282,382

[22] Filed: Dec. 9, 1988

[30] Foreign Application Priority Data

Dec. 11, 1987 [FR] France .................... 87 17296

[51] Int. Cl.$^5$ ............................. C07C 45/58
[52] U.S. Cl. .................... 568/486; 560/124; 568/485
[58] Field of Search ............ 560/124; 568/486, 485

[56] References Cited

U.S. PATENT DOCUMENTS 4,551,545 11/1985 Frank-Neumann et al. ........ 560/124

FOREIGN PATENT DOCUMENTS 3229537 2/1984 Fed. Rep. of Germany ...... 560/124

OTHER PUBLICATIONS

Mulzer et al., "Chemical Abstracts", vol. 98 (1983), 160,949t.
Mulzer et al., "Chemical Abstracts", vol. 101 (1984) 23776a.

Primary Examiner—Werren B. Lone
Attorney, Agent, or Firm—Bierman and Muserlian

[57] ABSTRACT

A novel process for the preparation of compounds of the formula

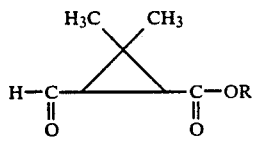

with cis or trans structure in racemic or optically active form wherein R is selected from the group consisting of hydrogen, alkyl of 1 to 4 carbon atoms and aryl of 6 to 12 carbon atoms comprising reacting an optically active isomer, or racemate of the formula

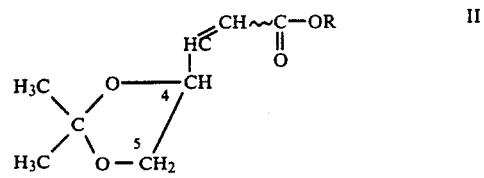

wherein R has the above definition and the way line indicates Z or E geometry with a gem-dimethyl cyclopropanation agent if there is Z geometry to obtain a compound of the formula

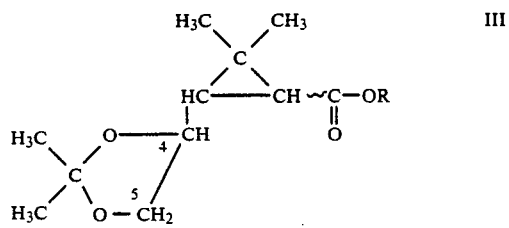

or if the geometry is E with a gem-dimethyl cyclopropanation agent other than isopropylidene triphenyl phosphorane to obtain a compound of the formula

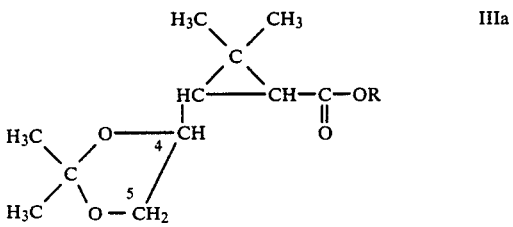

wherein R has the above definition and the cyclopropane ring has the trans configuration and either hydrolyzing the compound of formula III or IIIa to obtain a compound of the formula

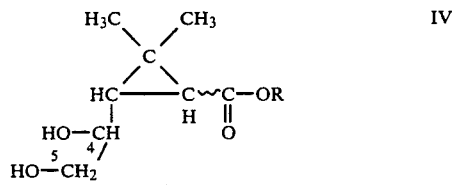

and then cleaving the 4,5 bond to obtain the corresponding compound of formula I or simultaneously cleaving the 4,5 bond and hydrolyzing the dioxolane group to obtain the corresponding compound of formula I and novel intermediates.

19 Claims, No Drawings

PROCESS FOR PREPARING SEMI-CARONIC ALDEHYDES

STATE OF THE ART

German Pat. No. 3,229,537 describes a related process.

OBJECTS OF THE INVENTION

It is an object of the invention to provide a novel process for the preparation of compounds of formula I and novel intermediates.

This and other objects and advantages of the invention will become obvious from the following detailed description.

THE INVENTION

The novel process of the invention for the preparation of the formula

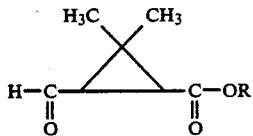

with cis or trans structure in racemic or optically active form wherein R is selected from the group consisting of hydrogen, alkyl or 1 to 4 carbon atoms and aryl of 6 to 12 carbon atoms comprises reacting an optically active isomer, or racemate of the formula

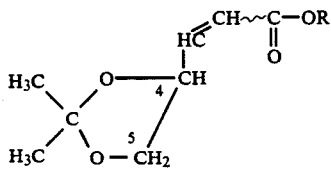

wherein R has the above definition and the wavy line indicates Z or E geometry with a gem-dimethyl cyclopropanation agent if there is Z geometry to obtain a compound of the formula

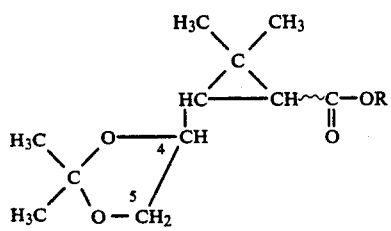

or if the geometry is E with a gem-dimethyl cyclopropanation agent other than isopropylidene triphenyl phosphorane to obtain a compound of the formula

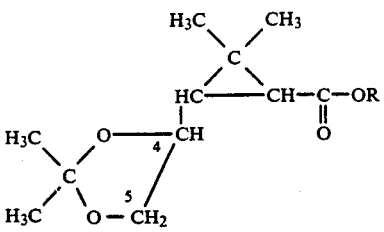

wherein R has the above definition and the cyclopropane ring has the trans configuration, and either hydrolyzing the compound of formula III or IIIa to obtain a compound of the formula

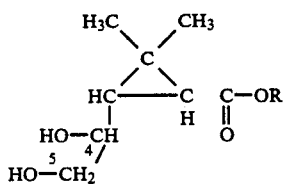

and then cleaving the 4,5 bond to obtain the corresponding compound of formula I or simultaneously cleaving the 4,5 bond and hydrolyzing the dioxolane group to obtain the corresponding compound of formula I. Examples of R are methyl, ethyl, n-propyl, isopropyl, n-butyl and branched butyls.

In a preferred mode of the process of the invention, the gem-dimethyl cyclopropanation agent when the compound of formula II has Z geometry is

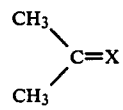

wherein X is —P—(Ar)$_3$, —S—(Ar)$_2$, —As—(Ar)$_3$ or

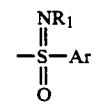

wherein Ar is aryl, especially phenyl and R$_1$ is hydrogen or alkyl of 1 to 4 carbon atoms or when the compound of formula II has E geometry, the gem-dimethyl cyclopropanation agent is

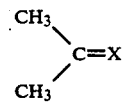

wherein X is S(Ar)$_2$. The hydrolysis of the dioxolane group is effected with a mineral or organic acid such as hydrochloric acid, sulfuric acid, acetic acid, perchloric acid or p-toluene sulfonic acid. The cleavage of the 4,5-bond may be effected with an oxidizing agent such as periodate, lead tetraacetate or potassium permanganate. The simultaneous hydrolysis of the dioxolane group and the 4,5-bond cleavage is preferably effected with periodic or periodate in the presence of sulfuric acid.

A preferred mode of the process of the invention for the preparation of a compound of the formula

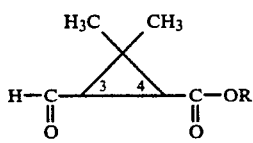  I$_A$ of trans structure, racemic or optically active wherein R is defined as previously comprises reacting the compound of formula II in any one of its isometic forms, racemic or optically active with the geometry of the double bond being Z with isopropylidene triphenyl phosphorane, or with the geometry of the double bond being E with a gem-dimethyl cyclopropanation agent other than isopropylidene triphenyl phosphorane to obtain a compound of the formula

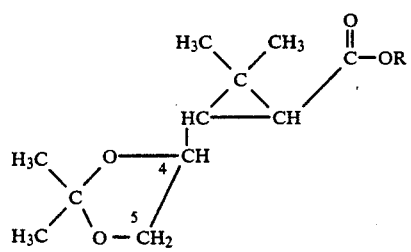  IIIa wherein R has the above definitions and the cyclopropane ring has trans configuration and either hydrolyzing the latter to obtain a compound of the formula

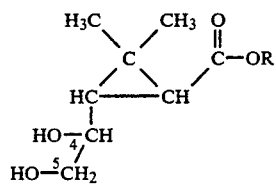  IVa wherein R and the configuration of the cyclopropane cycle are as above and the bond 4,5 is cleaved to obtain the compound of formula I$_A$, or the dioxolane residue is hydrolyzed and the 4,5 bond is simultaneously cleaved to obtain the compound of formula I$_A$.

Another preferred mode of the process of the invention for the preparation of a compound of the formula

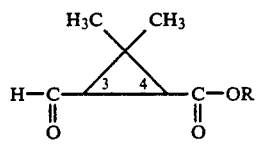  I$_B$ of cis structure, racemic or optically active wherein R is defined as above comprises reacting a compound of the formula

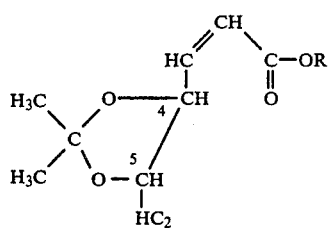  II' wherein R has the above definitions and the geometry of the double bond is Z with isopropylidene diphenyl sulfurane to obtain a compound of the formula

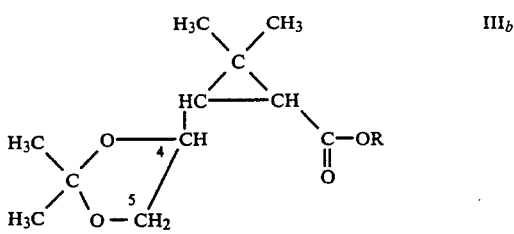  III$_b$ wherein R is defined as above and the configuration of the cyclopropane ring is cis and either the dioxolane residue is hydrolyzed to obtain a compound of the formula

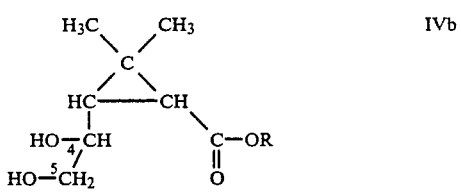  IVb wherein R and the configuration of the cyclopropane ring are defined as above and the 4,5 bond is cleaved to obtain the compound of formula I$_B$, or the dioxolane residue is hydrolyzed and the 4,5 bond are simultaneously cleaved to obtain the compound of the formula I$_B$.

A preferred process for the preparation of compounds of formula I$_B$ with a (1R,cis) configuration comprises reacting a compound of the formula

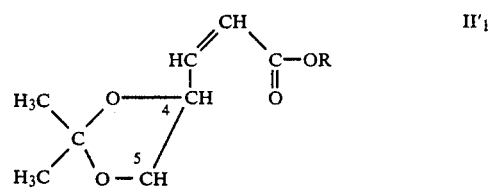  II'$_1$ of configuration (4S) wherein R has the above definition and the geometry of the double bond is Z with isopropylidene diphenyl sulfurane to obtain a compound of the formula

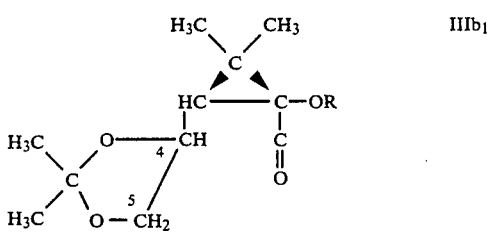  IIIb$_1$ of (4S) and (1R,cis) configuration at the cyclopropane level and either the dioxolane residue is hydrolyzed to obtain a compound of the formula

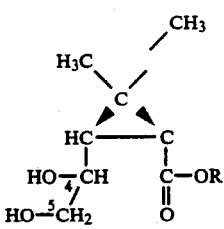

of (4S) configuration and (1R,cis) at the cyclopropane ring wherein R has the above definition and the 4,5 bond is cleaved by the action of an oxidizing agent to obtain a compound of formula IB of (1R,cis) configuration or the dioxolane residue is hydrolyzed and the 4,5 bond is simultaneously cleaved to obtain a compound of formula (IB) of (1R,cis) configuration.

A preferred mode of the process of the invention for the preparation of a compound of formula $I_A$ with trans configuration comprises reacting a compound of the formula

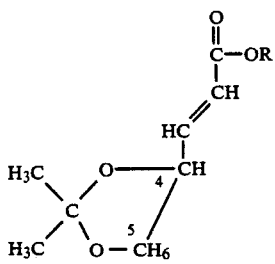

of (4R) configuration wherein R has the above definition and the geometry of the double bond is E with an isopropylidene diphenyl sulfurane to obtain a compound of the formula

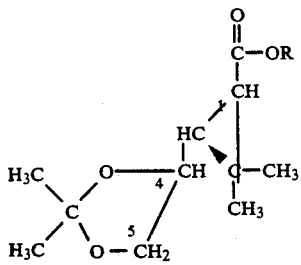

of (4R) configuration and (1R,trans) at the cyclopropane ring is which R is defined as above and either the dioxolane residue is hydrolyzed to obtain a compound of the formula

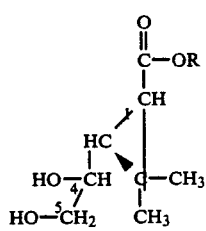

of (4R) configuration and (1R,trans) at the cyclopropane ring wherein R is defined as above and the 4,5 bond is cleaved by the action of an oxidizing agent to obtain a compound of formula IA of (1R,trans) configuration, or the dioxolane residue is hydrolyzed and simultaneously the 4,5 bond is cleaved to obtain a compound of formula IA of (1R,trans) configuration.

More particularly, the subject of the invention is a process for the preparation of the compound of formula IA of (1R,trans) configuration comprising reacting a compound of the formula

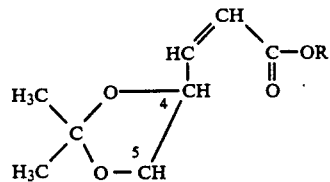

of (4R) configuration in which R is defined as above and the geometry of the double bond is Z with isopropylidene triphenyl phosphorane to obtain a compound of formula $IIIa_1$ as defined above and then the synthesis is continued as above to obtain the expected product of formula IA of (1R,trans) configuration.

In addition to the compounds of the structural formula (1R,cis), depending on the configuration at position 4 of the starting compound of formula II and depending on the configuration of the double bond of the compounds of formula II, the invention process permits enantioselective access to all the possible isometic structures with the formula I.

In the Table below, there are illustrated the configurations obtained of the compounds of formula I of cis or trans geometry as well as of the isolated intermediates, starting with chiral compounds of formula II using either isopropylidene triphenylphosphorance, or isopropylidene diphenylsulfurane; for convenience, the configuration of the starting glyceraldehyde acetonide is also shown.

| Reagent | Glyceraldehyde Acetonide | Compound (II) | Compound (III) | Compound (I) |
|---|---|---|---|---|
| ∅₃P= | D (or R) | 4S.E | 1R trans 4S | 1R trans |
|  | " | 4S.Z | 1S trans 4S | 1S trans |
|  | L (or S) | 4R.E | 1S trans 4R | 1S trans |
|  | " | 4R.Z | 1R trans 4R | 1R trans |
| ∅₃S= | D (or R) | 4S.E | 1S trans 4S | 1S trans |
|  | " | 4S.Z | 1R cis 4S | 1R cis |
|  | L (or S) | 4R.E | 1R trans 4R | 1R trans |
|  | " | 4R.Z | 1S cis 4R | 1S cis |

The invention has also for its object the compounds of formulae IIIb and IVb obtained during the putting into operation of the preparation process for the compounds of formula I of cis structure.

The compounds of formula I are known under the name of semi-caronic aldehydes and are useful intermediates in the synthesis of chrysanthemic acid or of its analogues, notably those halogenated. The esters of formula II are known compounds, which can be obtained starting from glyceraldehyde acetonide. For example, the starting compounds of formula II may be prepared by known processes described by Minami et al, J.A.C.S., (1982), Vol. 104, p. 1109 and Mulzer et al, Angew. Int. Ed. 1983, Vol. 22, p. 63 for instances.

In the following examples there are described several preferred embodiments to illustrate the invention. However, it should be understood that the invention is not intended to be limited to the specific embodiments.

EXAMPLE 1

Methyl (1R,cis) 3-formyl-2,2-dimethylcyclopropane carboxylate

STEP A: [(4S) 2,2-dimethyl-1,3-diololan-4-yl]-3-[methyl 2,2-dimethyl 1R,3S-cyclopropane-carboxylate]

A solution of 0.574 g of isopropyldiphenylsulfonium tetrafluoroborate and 0.128 g of anhydrous dichloromethane in 12 ml of anhydrous dimethoxyethane was cooled to −78° C. under the inert gas, and a solution of lithium diisopropylamide obtained by treatment for 15 minutes at −78° C. of 0.172 g of diisopropylamine in 5 ml of dimethoxyethane by 1.05 ml of n-butyllithium (1.55 M in hexane) was added. After stirring at −78° C. for 15 minutes, a solution of 0.186 g of [(4S) 2,2-dimethyl-1,3-dioxolan-4-yl]-3(Z)-methyl propenoate in 2 ml of dimethoxyethane was added. The reaction mixture was stirred for 15 minutes at −78° C., then for 45 minutes between −65° and −50° C. and finally it was allowed to heat up. 5 ml of water were added and the organic phase was diluted with ether. The aqueous phase was separated and the organic phase was washed with water and dried. The evaporation of the solvents under vacuum yielded 0.4 g of crude product which was chromatographed on silica and eluted with a pentane-ether (75-25) mixture to obtain 0.192 g of the expected product with a specific rotation of $[\alpha]_D^{20} = -15.04°$ (c=18.75% in $CHCl_3$).

NMR Spectrum ($CCl_4$):

Delta 0.9–1.8 (m, 14H, $CH_3$ and H on the cyclopropane); 3.2–3.65 (m with s at 3.6 $CO_2CH_3$), 4H, $CO_2CH_3$ and one of the H of the dioxolane); 3.95 (dd, 1H, one of the H of the dioxolane); 4.25–4.66 (m, 1H, one of the H of the dioxolane).

STEP B: Methyl (1R,cis) 3-formyl-2,2-dimethylcyclopropane carboxylate 0.15 g of the product of Step A were dissolved in 8 ml of THF and at 20° C., 4 ml of an aqueous solution of 2.5 M perchloric acid were added. The mixture was stirred for 3 hours at 20° C. and solid sodium bicarbonate was then added until a basic pH was obtained. Then, the reaction mixture was extracted with ether and the organic phase was dried and evaporated to dryness under vacuum. The crude diol obtained was used as is for the following step.

The crude diol was dissolved in 6 ml of methanol and 3 ml of phosphate buffer (ph:7.2), and treated with an excess of sodium periodate (that is, 0.214 g) added in one lot at 20° C. After stirring for 30 minutes at 20° C., the methanol was evaporated under vacuum. The residue was stirred in the presence of 60 ml of ether and the organic phase was decanted, washed with 5 ml of water and dried. After evaporation of the solvents under vacuum, the crude mixture was purified by chromatography on silica gel to obtain 0.06 g of the expected product with a specific rotation of $[\alpha]_D^{20} = -76.4°$ (c=16.9 mg/ml in acetone).

EXAMPLE 2

Methyl (1R,trans) 3-formyl-2,3-dimethylcyclopropane carboxylate

STEP A: [(4R) 2,2-dimethyl-1,3-dioxolane-4-yl]-3-[methyl 2,2-dimethyl-1R,3R-cyclopropane carboxylate]

Using the procedure of Step A of Example 1, 0.186 g of methyl[(4R) 2,2-dimethyl-1,3-dioxolane-4-yl]-3E-propenoate were reacted and after chromatography on silica and elution with a (7-3)pentane-ether mixture, 0.21 g of the expected product were obtained.

NMR Spectrum ($CCl_4$):

Delta 1.70–0.9 (m with 2s at 1.2 and 1.35, 12H, $CH_3$ and cyclopropane CH); 3.8–4.25 (m with s at 3.8, 6H, $CO_2CH_3$, CH-O and $CH_2O$).

STEP B: Methyl (1R,trans) 3-formyl-2,2-dimethylcyclopropane carboxylate

Using the procedure of Step B of Example 1, 0.15 g of the product of Step A were reacted to obtain 0.065 g of the expected product with a specific rotation of $[\alpha]_D^{20} = +13.6°$ (c=11.5 mg/ml acetone).

EXAMPLE 3

Methyl (1R,trans) 3-formyl-2,2-dimethylcyclopropane carboxylate

STEP A: [(4R) 2,2-dimethyl-1,3-dioxolan-4-yl]-3-[methyl 2,3-dimethyl-1R,3R-cyclopropane carboxylate]

A (1.5 $10^{-3}$M) solution was prepared consisting of triphenylisopropylidene phosphorane in tetrahydrofuran by adding a solution of n-butyllithium in hexane to a suspension of isopropyltriphenylphosphonium iodide in tetrahydrofuran. At 0° C. 6 ml of the said solution were introduced into 0.186 g of methyl [(4R) 2,2-dimethyl-1,3-dioxolan-4-yl]-3-(Z)-propenoate dissolved in 4 ml of tetrahydrofuran and the mixture was stirred for 1 hour at 0° C., then for 1 hour after returning to 20° C. The reaction medium was diluted with 5 ml of water and extracted with ether. The organic phase was dried, and the solvents were eliminated under reduced pressure to obtain 0.25 g of crude product. After purification by chromatography on silica, (eluent, pentane-ether, 8-2), 0.15 g of the expected product were obtained.

NMR Spectrum ($CCl_4$):

H of $CO_2CH_3$, —CH—O and —$CH_2$—O: 4.25 to 3.8 ppm(m); H of the methyl and cyclopropane H: 1.7 to 0.9 ppm(m).

STEP B: Methyl (1R,trans) 3-formyl-2,2-dimethylcyclopropane carboxylate

Using the procedure of Step B of Example 1, 0.15 g of the product of Step A were reacted to obtain 0.085 g of crude product which was chromatographed on silica and eluted with a 7-3 pentane-ether mixture to obtain the expected product with a specific rotation of $[\alpha]_D^{20} = +13.6°$ (c=11.5 mg/ml in acetone).

EXAMPLE 4

Methyl (1S-trans) 3-formyl-2,2-dimethylcyclopropane carboxylate

STEP A: [(4S) 2,2-dimethyl-1,3-dioxolan-4-yl]-3-[methyl 2,2-dimethyl-1S,3S-cyclopropane carboxylate]

Using the procedure of Example 3, 0.186 g of [(4S) 2,2-dimethyl-1,3-dioxolan-4-yl]-methyl-3(Z)-propenoate were reacted to obtain after purification, 0.15 g of the expected product with a specific rotation of $[\alpha]_D^{20} = +37.5°$ (c=13 mg/ml in acetone).

STEP B: Methyl (1S,trans) 3-formyl-2,2-dimethylcyclopropane carboxylate

Using the procedure of Step B of Exampe 1, 0.15 g of the product of Step A were reacted to obtain 0.08 g of crude product which was purified by chromatography on silica and elution with a 7-3 pentane-ether mixture to obtain the expected product with a specific rotation of $[\alpha]_D^{20} = -18.8°$ (c=13 mg/ml in acetone).

Various modifications of the process of the products of the invention may be made without departing from the spirit or scope thereof and it is to be understood that the invention is intended to be limited only defined in the appended claims.

What is claimed is:

1. A process for the preparation of compounds of the formula

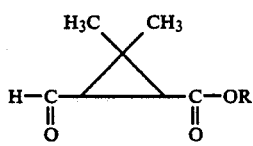

with cis or trans structure in racemic or optically active form wherein R is selected from the group consisting of hydrogen, alkyl of 1 to 4 carbon atoms and aryl of 6 to 12 carbon atoms comprising reacting an optically active isomer, or racemate of the formula

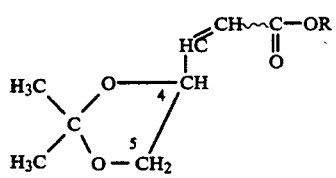

wherein R has the above definition and the wavy line indicates Z geometry with a gem-dimethyl cyclopropanation agent of the formula

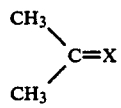

wherein X is selected from the group consisting of —P-(Ar)₃, S(Ar)₂, Se(Ar)₂, —As(Ar)₂ and

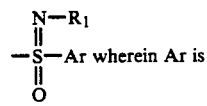

aryl and R₁ is hydrogen or alkyl of 1 to 5 carbon atoms to obtain a compound of the formula

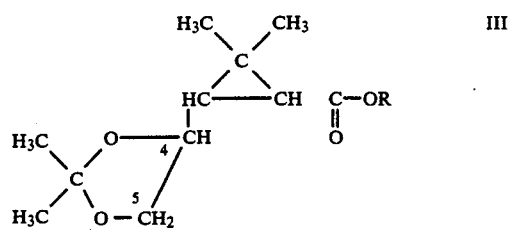

wherein R has the above definition and the cyclopropane ring has the trans configuration and hydrolyzing the compound of formula III with a mineral or organic acid to obtain a compound of the formula

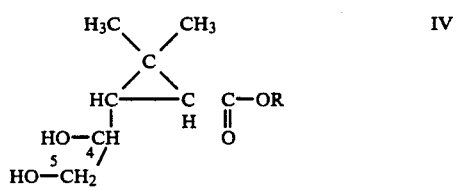

and then cleaving the 4,5 bond under oxidizing conditions to obtain the corresponding compound of formula I.

2. The process of claim 1 wherein the gem-dimethyl cyclopropanation agent of formula II with Z geometry has the formula

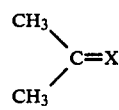

wherein X is selected from the group consisting of P(Ar)₃, S(Ar)₂, Se(Ar)₂, As(Ar)₃ and

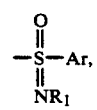

R₁ is hydrogen or alkyl of 1 to 4 carbon atoms and Ar is aryl.

3. The process of claim 2 wherein Ar is phenyl.

4. A process for the preparation of a compound of the formula

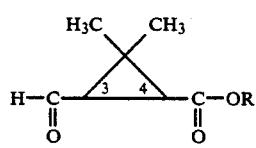

of cis structure, racemic or optically active wherein R is defined as above comprising reacting a compound of the formula

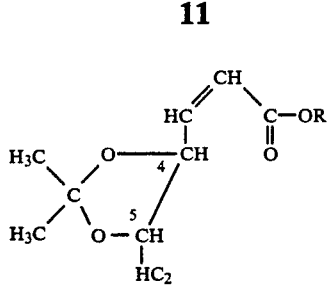

II' wherein R has the above definition and the geometry of the double bond is Z with isopropylidene diphenyl sulfurane, to obtain a compound of the formula

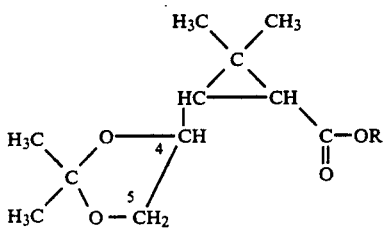

III$_b$ wherein R is defined as above and the configuration of the cyclopropane ring is cis and the dioxolane residue is hydrolyzed with a mineral or organic acid to obtain a compound of the formula

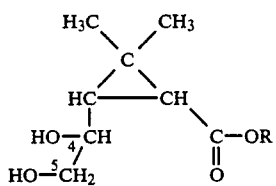

IVb wherein R and the configuration of the cyclopropane ring are defined as above and the 4,5 bond is cleaved under oxidizing conditions to obtain the compound of formula I$_B$.

5. A process for the preparation of compounds of formula I$_B$ with a (1R,cis) configuration comprising reacting a compound of the formula

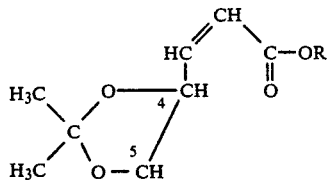

II'$_1$ of configuration (4S) where R has the above definition and the geometry of the double bond is Z with isopropylidene diphenyl sulfurane to obtain a compound of the formula

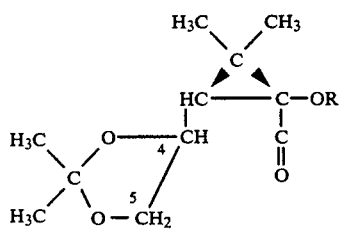

IIIb$_1$ of (4S) and (1R,cis) configuration at the cyclopropane level and the dioxolane residue is hydrolyzed with a mineral or organic acid to obtain a compound of the formula

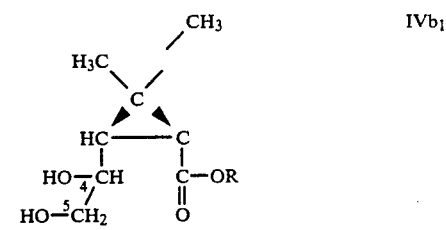

IVb$_1$ of (4S) configuration and (1R,cis) at the cyclopropane ring wherein R has the above definition and the 4,5 bond is cleaved under oxidizing conditions by the action of an oxidizing agent to obtain a compound of formula IB of (1R,cis) configuration.

6. A process for the preparation of a compound of formula I$_A$ with -1R trans configuration comprising reacting a compound of the formula

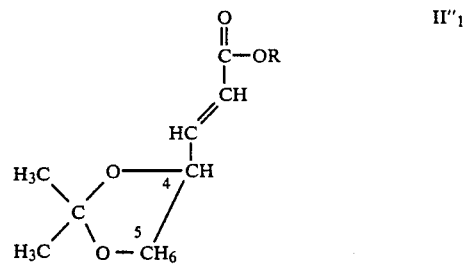

II''$_1$ of (4R) configuration wherein R has the above definition and the geometry of the double bond is E with an isopropylidene diphenyl sulfurane to obtain a compound of the formula

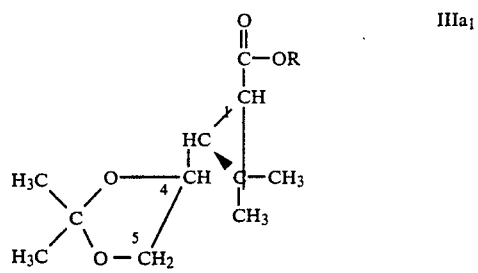

IIIa$_1$ of (4R) configuration and (1R,trans) at the cyclopropane ring in which R is defined as above and the dioxolane residue is hydrolyzed with a mineral or organic acid to obtain a compound of the formula

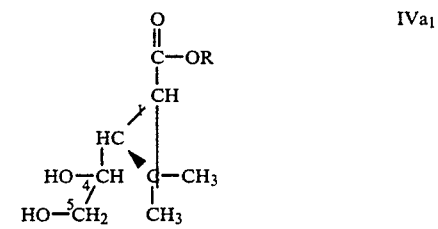

IVa$_1$ of (4R) configuration and (1R,trans) at the cyclopropane ring wherein R is defined as above and the 4,5 bond is cleaved under oxidizing conditions by the action of an oxidizing agent to obtain a compound of formula IA of (1R,trans) configuration.

7. A process for the preparation of the compound of formula IA of (1R,trans) configuration comprising reacting a compound of the formula

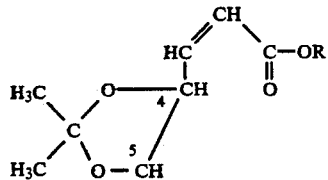

of (4R) configuration in which R is defined as in claim 1 and the geometry of the double bond is Z with isopropylidene triphenyl phosphorane to obtain a compound of formula IIIa₁ as defined in claim 6 and then the synthesis is continued as in claim 6 to obtain the expected product of formula IA of (1R,trans) configuration.

8. A compound having a formula selected from the group consisting of

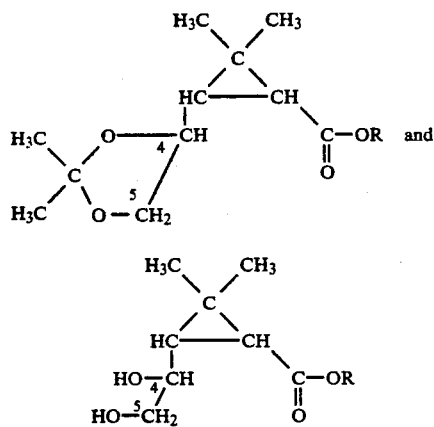

wherein R is as defined in claim 1 and the cyclopropane configuration is cis.

9. A process for the preparation of a compound of the formula

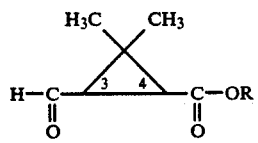

of cis structure, racemic or optically active wherein R is defined as above comprising reacting a compound of the formula

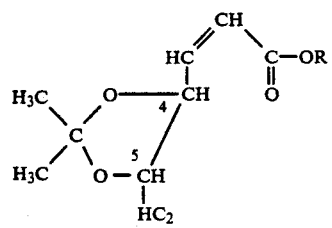

wherein R has the above definition and the geometry of the double bond is Z with isopropylidene diphenyl sulfurane to obtain a compound of the formula

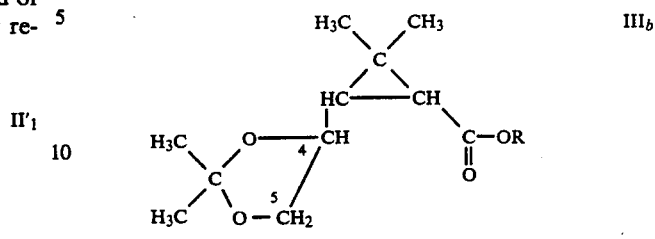

wherein R is defined as above and the configuration of the cyclopropane ring is cis and the dioxolane residue is hydrolyzed and the 4,5 bond are simultaneously cleaved with periodic acid or a periodate in the presence of sulfuric acid to obtain the compound of the formula $I_B$.

10. A process for the preparation of compounds of formula $I_B$ with a (1R,cis) configuration comprising reacting a compound of the formula

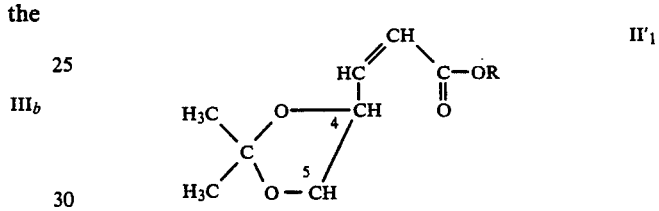

of configuration (4S) wherein R has the above definition and the geometry of the double bond is Z with isopropylidene diphenyl sulfurane to obtain a compound of the formula

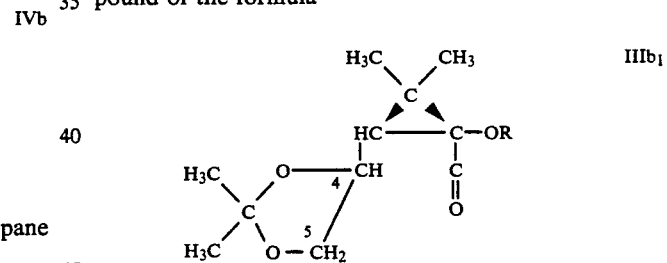

of configuration (4S) where R has the above definitions and the geometry of the double bond is Z with isopropylidene diphenyl sulfurane to obtain a compound of the formula

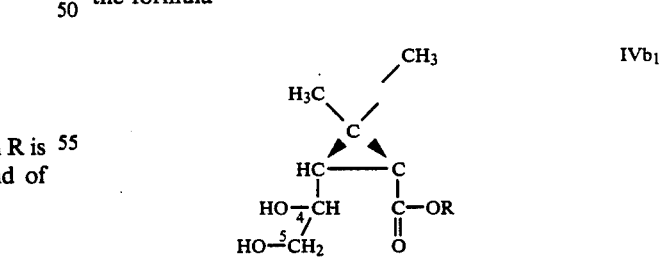

of (4S) and (1R,cis) configuration at the cyclopropane level and the dioxolane residue is hydrolyzed and the 4,5 bond is simultaneously cleaved with periodic acid or a periodate in the presence of sulfuric acid to obtain a compound of formula (1B) of (1R,cis) configuration.

11. A process for the preparation of a compound of formula $I_A$ with -1R trans configuration comprising reacting a compound of the formula

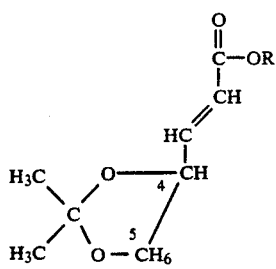

of (4R) configuration wherein R has the above definition and the geometry of the double bond is E with an isopropylidene diphenyl sulfurane to obtain a compound of the formula

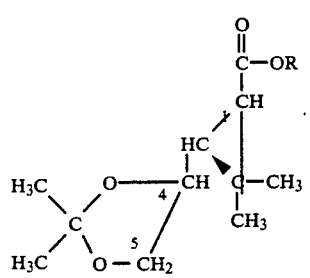

of (4R) configuration and (1R,trans) at the cyclopropane ring in which R is defined as above and the dioxolane residue is hydrolyzed and simultaneously the 4,5 bond is cleaved with periodic acid or a periodate in the presence of sulfuric acid to obtain a compound of formula 1 A of (1R,trans) configuration.

12. A process for the preparation of a compound of the formula

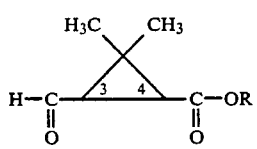

of trans structure, racemic or optically active wherein R is selected from the group consisting of hydrogen, alkyl or 1 to 4 carbon atoms and aryl of 6 to 12 carbon atoms comprising reacting the compound of formula II of claim 1 in any one of its isomeric forms, racemic or optically active with the geometry of
the double bond being Z with isopropylidene triphenyl phosphorane to obtain a compound of the formula

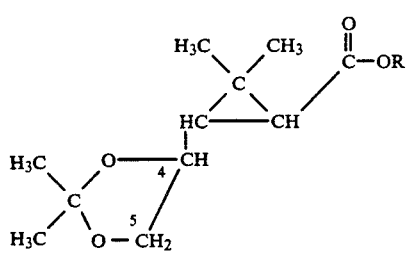

wherein R has the above definition and the cyclopropane ring has trans configuration and hydrolyzing the latter with a mineral or organic acid to obtain a compound of the formula

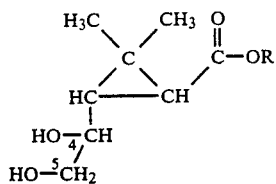

wherein R and the configuration of the cyclopropane cycle are as above and then cleaving the 4,5 bond under oxidizing conditions to obtain the compound of formula $I_A$.

13. A process for the preparation of compounds of the formula

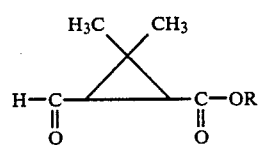

with cis or trans structure in racemic or optically active form wherein R is selected from the group consisting of hydrogen, alkyl of 1 to 4 carbon atoms and aryl of 6 12 carbon atoms comprising reacting an optically active isomer, or racemate of the formula

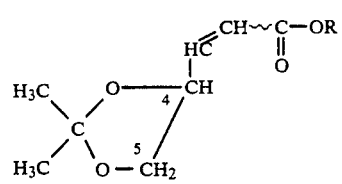

wherein R has the above definition and the wavy line indicates Z geometry with a gem-dimethyl cyclopropanation agent of the formula

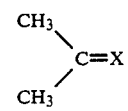

wherein X is selected from the group consisting of —P-(Ar)$_3$, S(Ar)$_2$, Se(Ar)$_2$, —As(Ar)$_2$ and

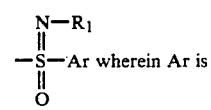

aryl and R$_1$ is hydrogen or alkyl or 1 to 4 carbon atoms to obtain a compound of the formula

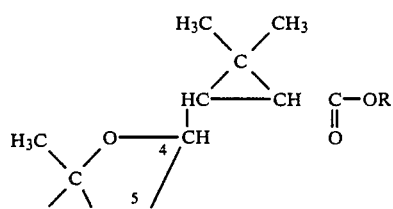

wherein R has the above definition and the cyclopropane ring has the cis or trans configuration and simultaneously cleaving the 4,5 bond and hydrolyzing the dioxolane group with periodic acid or a periodate int he presence of sulfuric acid to obtain the corresponding compound of the formula I.

14. A process for the preparation of a compound of the formula

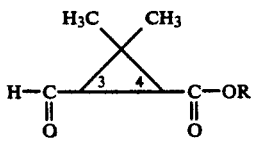

of trans structure, racemic or optically active wherein R is selected from the group consisting of hydrogen, alkyl of 1 to 4 carbon atoms and aryl of 6 to 12 carbon atoms comprising reacting the compound of formula II of claim 1 in any one of its isomeric forms, racemic or optically active with the geometry of the double bond being Z with isopropylidene triphenyl phosphorane to obtain a compound of the formula

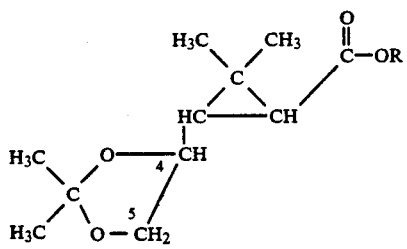

wherein R has the above definition and the cyclopropane ring has trans configuration and the dioxolane residue is hydrolyzed and the 4,5 bond is simultaneously cleaved with periodic acid or a periodate in the presence of sulfuric acid to obtain the compound of formula $I_A$.

15. A process for the preparation of compounds of the formula

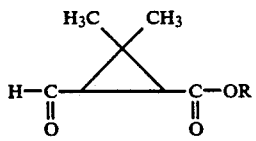

with trans structure in racemic or optically active form wherein R is selected from the group consisting of hydrogen, alkyl of 1 to 4 carbon atoms and aryl of 6 to 12 carbon atoms comprising reacting an optically active isomer, or racemate of the formula

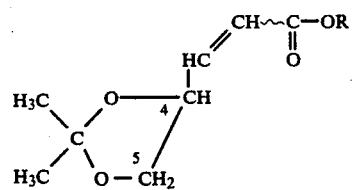

wherein R has the above definition and the wavy line indicates E geometry with a gem-dimethyl cyclopropanation agent of the formula

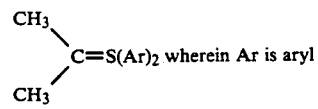

to obtain a compound of the formula

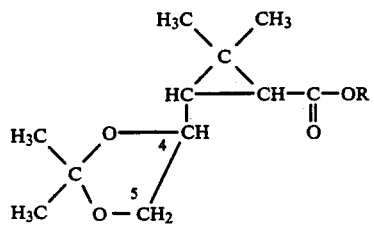

wherein R has the above definition and the cyclopropane ring has the trans configuration and hydrolyzing the compound of formula IIIa with a mineral or organic acid to obtain a compound of the formula

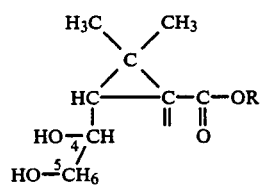

and then cleaving the 4,5 bond under oxidizing conditions to obtain the corresponding compound of formula $I_A$.

16. The process for the preparation of a compound of the formula

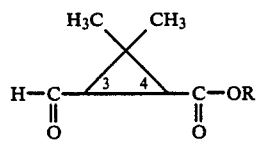

of trans structure, racemic or optically active wherein R is selected from the group consisting of hydrogen, alkyl of 1 to 4 carbon atoms and aryl of 6 to 12 carbon atoms comprising reacting the compound of formula II of claim 1 in any one of its isomeric forms, racemic or optically active with the geometry of the double bond being E with isopropylidene diphenyl sulfurane to obtain a compound of the formula

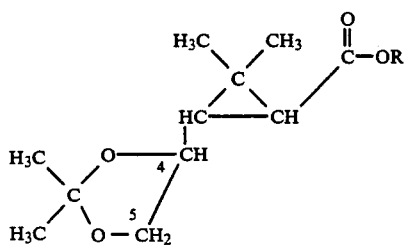

wherein R has the above definition and the cyclopropane ring has trans configuration and hydrolyzing the latter with a mineral or organic acid to obtain a compound of the formula

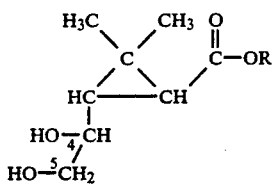

IVa wherein R and the configuration of the cyclopropane cycle are as above and then cleaving the 4,5 bond under oxidizing conditions to obtain the compound of formula $I_A$.

17. A process for the preparation of compounds of the formula

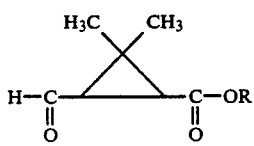

$I_A$ with trans structure in racemic or optically active form wherein R is selected from the group consisting of hydrogen, alkyl 1 to 4 carbon atoms and aryl of 6 to 12 carbon atoms comprising reacting an optically active isomer, or racemate of the formula

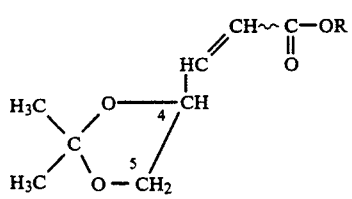

II wherein R has the above definition and the wavy line indicates E geometry with a gem-dimethyl cyclopropane agent of the formula

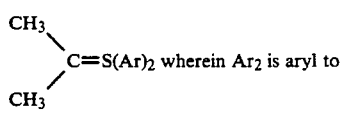

$C=S(Ar)_2$ wherein $Ar_2$ is aryl to obtain a compound of the formula

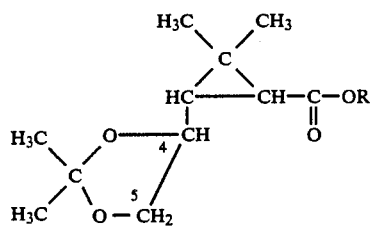

IIIa wherein R has the above definition and the cyclopropane ring has the trans configuration and simultaneously cleaving the 4,5 bond and hydrolyzing the dioxolane group with periodic acid or a periodate in the presence of sulfuric acid to obtain the corresponding compound of formula $I_A$.

18. A process for the preparation of a compound of the formula

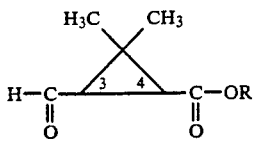

$I_A$ of trans structure, racemic or optically active wherein R is selected from the group consisting of hydrogen, alkyl of 1 to 4 carbon atoms and aryl of 6 to 12 carbon atoms comprising reacting the compound of formula II of claim 1 in any one of its isomeric forms, racemic or optically active with the geometry of the double bond being E with isopropylidene diphenyl sulfurane to obtain a compound of the formula

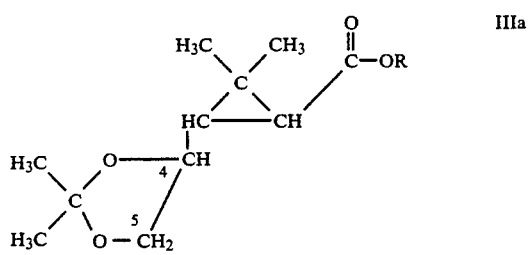

IIIa wherein R has the above definition and the cyclopropane ring has trans configuration and the dioxolane residue is hydrolyzed and the 4,5 bond is simultaneously cleaved with periodic acid or a periodate in the presence of sulfuric acid to obtain the compound of formula $I_A$.

19. A process for the preparation of a compound of the formula

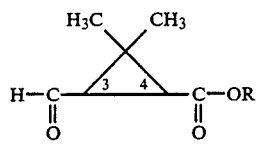

$I_A$ of (1R,trans) configuration wherein R is selected from the group consisting of hydrogen, alkyl of 1 to 4 carbon atoms and aryl of 6 to 12 carbon atoms comprising reacting a compound of the formula

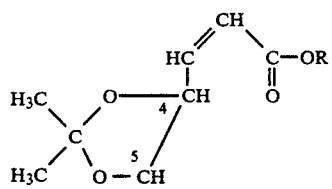

II'₁ of (4R) configuration wherein R is defined as above and the geometry of the double bond is Z with isopropylidene triphenyl phosphorane to obtain a compound of Formula III$_{a1}$ as defined in claim 6 and subjecting the latter to simultaneous hydrolysis and cleavage of the 4,5-bond with periodic acid or a periodate in the presence of sulfuric acid to obtain the corresponding compound of Formula $I_a$.

* * * * *

UNITED STATES PATENT AND TRADEMARK OFFICE
CERTIFICATE OF CORRECTION

PATENT NO. : 5,004,840
DATED : April 2, 1991
INVENTOR(S) : ALAIN KRIEF, WILLY DUMONT It is certified that error appears in the above-identified patent and that said Letters Patent is hereby corrected as shown below:

Col.  Line 4     45   Formula II$_1'$       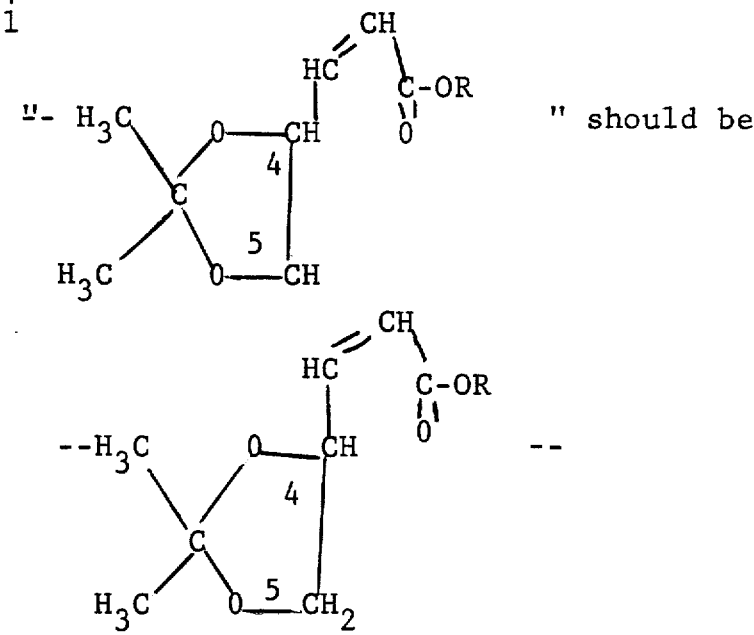      " should be 6     15 Formula II$_1'$          same as above
6     49                          "$O_3S=<$" should be --$O_2S=<$
9 Claim 1 line 67 & 68   "-P-(Ar)$_3$," should be -- -P(Ar)$_3$,--
10 Claim 1 line 8        "1 to 5 carbon atoms" should be
                         --1 to 4 carbon atoms--

UNITED STATES PATENT AND TRADEMARK OFFICE
CERTIFICATE OF CORRECTION

PATENT NO. : 5,004,840
DATED : April 2, 1991
INVENTOR(S) : ALAIN KRIEF, WILLY DUMONT It is certified that error appears in the above-identified patent and that said Letters Patent is hereby corrected as shown below:

Col.   Line

13     Claim 7   same in Col. 4 line 45

14     Claim 10   " " " " " " " " "

L)     Claim 1 Formula IV

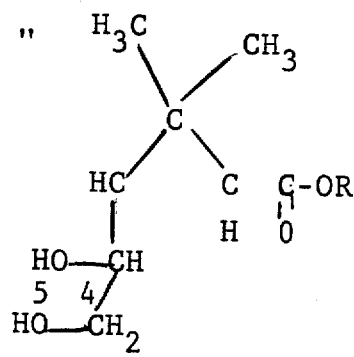

should be

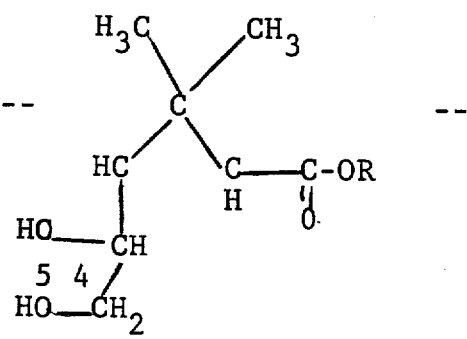

UNITED STATES PATENT AND TRADEMARK OFFICE
CERTIFICATE OF CORRECTION

PATENT NO. : 5,004,840
DATED : April 2, 1991
INVENTOR(S) : ALAIN KRIEF, WILLY DUMONT It is certified that error appears in the above-identified patent and that said Letters Patent is hereby corrected as shown below:

Col. line

16    Claim 13, line 47&48    " $-P-(Ar)_3$," should be -- $-P(Ar)_3$,--

Signed and Sealed this

Fifteenth Day of September, 1992

Attest:

DOUGLAS B. COMER

Attesting Officer    Acting Commissioner of Patents and Trademarks